(12) United States Patent
Sonderegger et al.

(10) Patent No.: US 11,612,723 B2
(45) Date of Patent: Mar. 28, 2023

(54) NEEDLE COVER RETENTION

(71) Applicant: Becton, Dickinson and Company, Franklin Lakes, NJ (US)

(72) Inventors: Ralph L. Sonderegger, Farmington, UT (US); Corey Christensen, Anaheim, CA (US); Bryan F. Bihlmaier, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 105 days.

(21) Appl. No.: 16/694,774

(22) Filed: Nov. 25, 2019

(65) Prior Publication Data
US 2020/0164180 A1 May 28, 2020

Related U.S. Application Data

(60) Provisional application No. 62/772,482, filed on Nov. 28, 2018.

(51) Int. Cl.
*A61M 25/06* (2006.01)
*A61M 25/00* (2006.01)

(52) U.S. Cl.
CPC .... *A61M 25/0631* (2013.01); *A61M 25/0054* (2013.01); *A61M 2025/0058* (2013.01); *A61M 2025/0098* (2013.01)

(58) Field of Classification Search
CPC .......... A61M 25/0631; A61M 25/0612; A61M 25/0618; A61M 2025/0681; A61M 2025/0098; A61M 2025/006; A61M 25/002
See application file for complete search history.

(56) References Cited

U.S. PATENT DOCUMENTS

| | | | | |
|---|---|---|---|---|
| 2003/0125713 A1* | 7/2003 | McGlinch | ........... | A61M 25/002 604/533 |
| 2005/0061697 A1* | 3/2005 | Moberg | ................ | A61F 2/0095 206/364 |
| 2014/0081210 A1* | 3/2014 | Bierman | ........... | A61M 25/0043 604/164.03 |
| 2014/0214005 A1* | 7/2014 | Belson | .............. | A61M 25/0606 604/510 |

* cited by examiner

*Primary Examiner* — Bhisma Mehta
*Assistant Examiner* — John J Crawford
(74) *Attorney, Agent, or Firm* — Kirton McConkie; Whitney Blair; Kevin Stinger

(57) ABSTRACT

A catheter assembly may include a catheter adapter, which may include a body and a nose extending distally from the body. The nose may be generally cylindrical. A strain relief rib may be disposed on the nose. The strain relief rib may be constructed of a flexible material. The catheter assembly may also include a needle secured within the catheter adapter and extending distally beyond the nose. The catheter assembly may further include a needle cover, which may be removably coupled to the nose of the catheter adapter. An inner surface of the needle cover may be smooth and may contact the strain relief rib.

8 Claims, 10 Drawing Sheets

NEEDLE COVER RETENTION

RELATED APPLICATIONS

This application claims the benefit of U.S. Provisional Application No. 62/772,482, filed Nov. 28, 2019, and entitled "NEEDLE COVER RETENTION", which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and the introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

There is a risk of accidental needle sticks if the distal tip of the introducer needle is not secured properly in a needle cover or shield. The present disclosure presents systems and methods to significantly limit and/or prevent needle sticks. The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. In some embodiments, a catheter assembly may include a catheter adapter, which may include a body and a nose extending distally from the body. In some embodiments, the nose may be generally cylindrical. In some embodiments, a strain relief rib may be disposed on the nose. In some embodiments, the strain relief rib may be constructed of a compliant or flexible material.

In some embodiments, the catheter assembly may include a catheter, which may be secured within the catheter adapter and may extend distally beyond the nose. In some embodiments, the catheter assembly may include a needle, which may be disposed within the catheter and may extend distal to a distal end of the catheter. In some embodiments, the catheter assembly may include a needle cover, which may be removably coupled to the nose of the catheter adapter. In some embodiments, the needle cover may be removably coupled to the distal end of the catheter adapter via a friction fit. In some embodiments, an inner surface of the needle cover may be smooth and may contact the strain relief rib. In some embodiments, the needle cover may be generally cylindrical and may include an open proximal end or a closed proximal end.

In some embodiments, the flexible material may include an elastomer. In some embodiments, the flexible material may include a thermoplastic elastomer. In some embodiments, the nose may be constructed of a rigid or semi-rigid material. In some embodiments, the strain relief rib may be generally aligned with a longitudinal axis of the catheter adapter. In some embodiments, the strain relief rib may be disposed on a bottom of the catheter adapter.

In some embodiments, a strain relief element may be disposed on a distal end of the nose. In some embodiments, the strain relief element may at least partially surround the needle and/or the catheter. In some embodiments, the strain relief element may be constructed of the flexible material or another flexible material. In some embodiments, the catheter adapter may include a stop configured to prevent proximal movement of the needle cover beyond the stop. In some embodiments, the stop may be proximate and proximal to the nose. In some embodiments, the strain relief rib may extend from the strain relief element to the stop.

In some embodiments, multiple strain relief ribs may be disposed on the nose. In some embodiments, the strain relief rib may be a first strain relief rib. In some embodiments, a second strain relief rib may be disposed on the nose and/or a third strain relief rib disposed on the nose. In some embodiments, the second strain relief rib and the third strain relief rib may be constructed of the flexible material or another flexible material. In some embodiments, the inner surface of the needle cover may contact the second strain relief rib and the third strain relief rib.

In some embodiments, the second strain relief rib and/or the third strain relief rib may be aligned with a longitudinal axis of the catheter adapter. In some embodiments, the second strain relief rib and/or the third strain relief rib may be disposed on an opposite side of the nose as the first strain relief rib. In some embodiments, the second strain relief rib and/or the third strain relief rib may be disposed on a top of the nose. In some embodiments, the second strain relief rib and/or the third strain relief rib extend from the strain relief element to the stop. In some embodiments, the first strain relief rib may be larger than the second strain relief rib and/or the third strain relief rib. In further detail, in some embodiments, a height of the first strain relief rib may be greater than a height of the second strain relief rib and/or the third strain relief rib. Additionally or alternatively, in some embodiments, a width of the first strain relief rib may be greater than a width of the second strain relief rib and/or the third strain relief rib.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
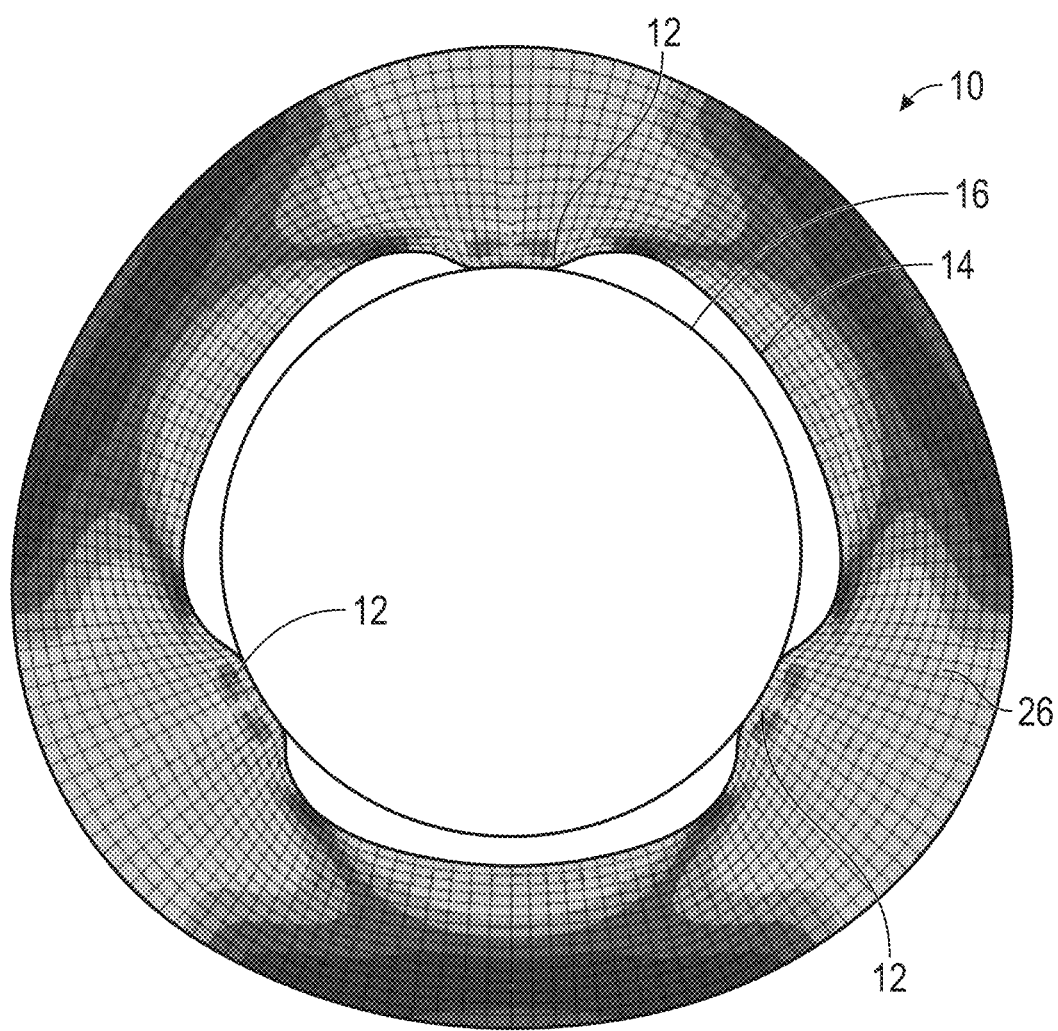
FIG. 1A is a finite element analysis of a cross-section of a prior art needle cover.
Figure 1B:
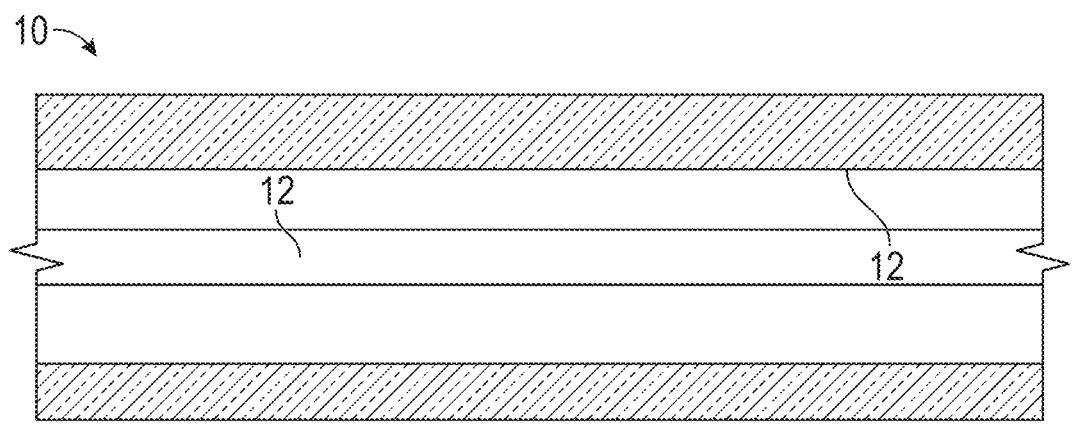
FIG. 1B is a longitudinal cross-sectional view of the prior art needle cover of FIG. 1A.

Referring now to FIG. 1A, a finite element analysis of a cross-section of a prior art needle cover 10 is illustrated. The prior art needle cover 10 has three internal lobes 12 that protrude from an inner surface 14 of the prior art needle cover 10. The prior art needle cover 10 and a catheter adapter 16 are coupled together in a press fit in which the internal lobes 12 contact and press upon an outer surface of a catheter adapter 16. Referring now to FIG. 1B, the internal lobes 12 may extend along a portion of the inner surface 14 of the prior art needle cover 10.

Figure 2A:
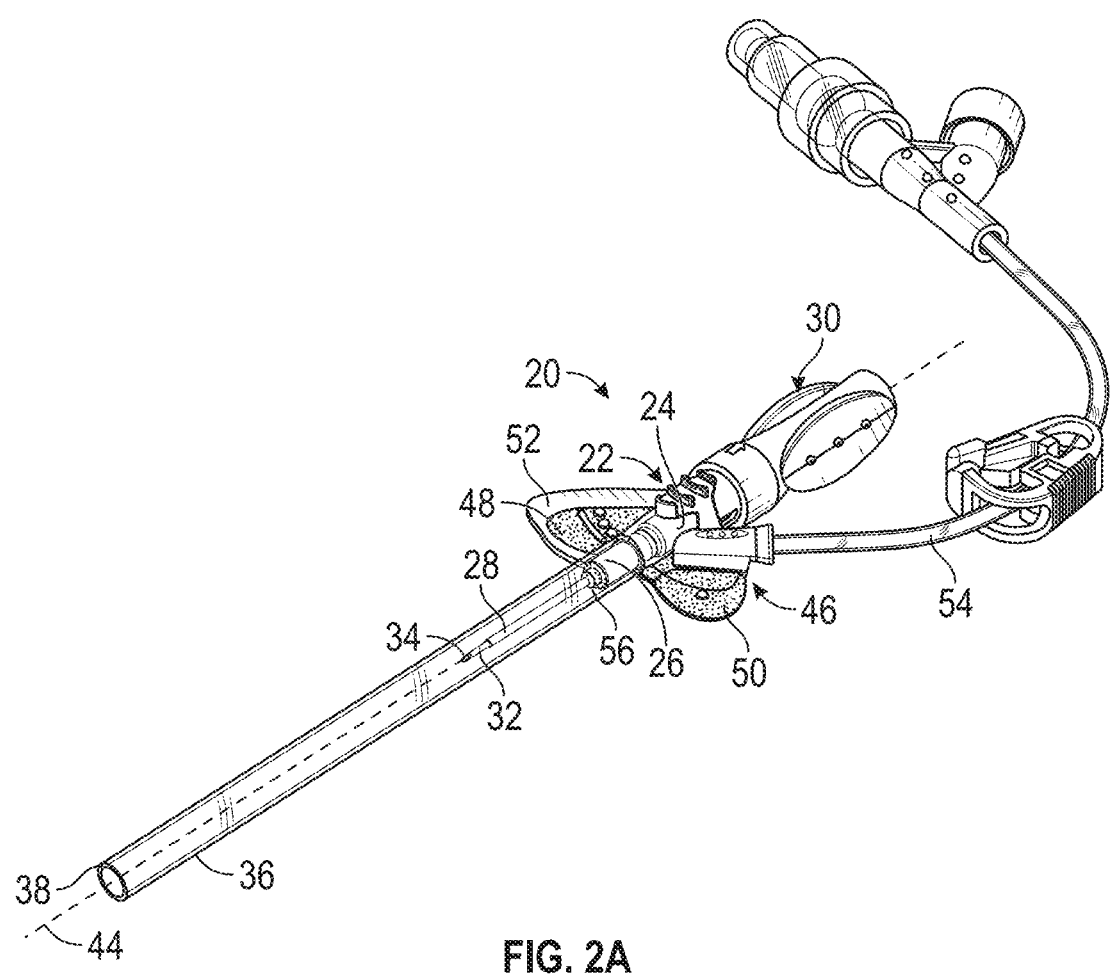
FIG. 2A is an upper perspective view of an example catheter assembly, illustrating an example needle cover shielding an example needle, according to some embodiments.

Referring now to FIG. 2A, an example catheter assembly 20 is illustrated, according to some embodiments. In some embodiments, the catheter assembly 20 may include a catheter adapter 22, which may include a body 24 and a nose 26 extending distally from the body 24. In some embodiments, the nose 26 may be generally cylindrical.

In some embodiments, the catheter assembly 20 may include a catheter 28, which may include a PIVC. In some embodiments, a proximal end of the catheter 28 may be secured within the catheter adapter 22. In some embodiments, the catheter 28 may extend distally beyond the nose 26.

In some embodiments, the catheter assembly 20 may include a needle assembly 30, which may be removably coupled to a proximal end of the catheter adapter 22. In some embodiments, the needle assembly 30 may include an introducer needle 32. In some embodiments, the introducer needle 32 may extend through the catheter 28.

In some embodiments, in response to the introducer needle 32 being inserted into a vasculature of a patient, flashback of blood may flow through a sharp distal tip 34 of the introducer needle 32 and may be visible to a clinician between the introducer needle 32 and the catheter 28 and/or at another location within the catheter assembly 20.

In some embodiments, in response to confirmation via the blood flashback that the catheter 28 is positioned within the vasculature of the patient, the needle assembly 30 may be removed from the catheter assembly 20. In some embodiments, when the needle assembly 30 is coupled to the catheter assembly 20, the introducer needle 32 of the needle assembly 30 may extend through a septum disposed within the lumen of the catheter adapter 22.

In some embodiments, the catheter assembly 20 may include a needle cover 36. In some embodiments, the needle cover 36 may be removably coupled to the distal end of the catheter adapter 22 via a friction fit. In some embodiments, the needle cover 36 may be removably coupled to the nose 26 of the catheter adapter 22 via a friction fit. In some embodiments, the needle cover 36 may be removed prior to insertion of the catheter 28 into the vasculature of the patient to expose the distal tip 34 of the introducer needle 32.

Figure 2B:
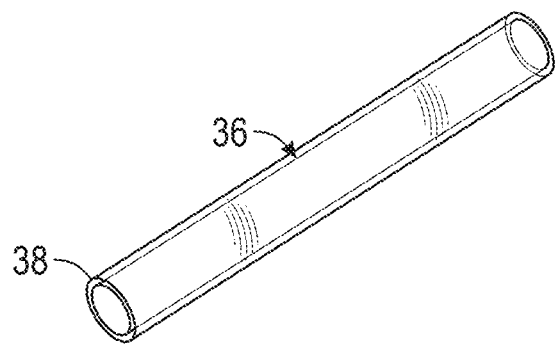
FIG. 2B is an upper perspective view of the needle cover of FIG. 2A, according to some embodiments.
Figure 2C:
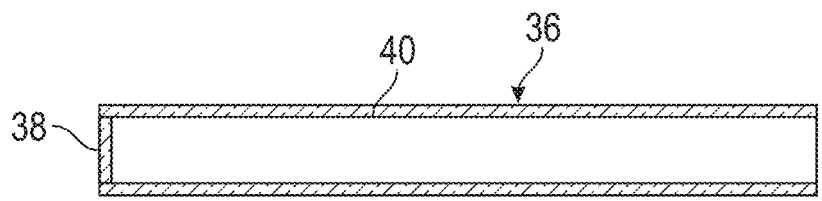
FIG. 2C is a cross-sectional view of the needle cover of FIG. 2A, according to some embodiments.

Referring now to FIGS. 2B-2C, in some embodiments, the needle cover 36 may be generally cylindrical. In some embodiments, the needle cover 36 may include a distal end 38, which may be closed as illustrated in FIG. 2C. In some embodiments, the distal end 38 of the needle cover 36 may be open. In some embodiments, an inner surface 40 of the needle cover 36 may be smooth, which may prevent the clinician or manufacturer from orienting the needle cover 36 to secure the needle cover 36 over the introducer needle 32.

Figure 3A:
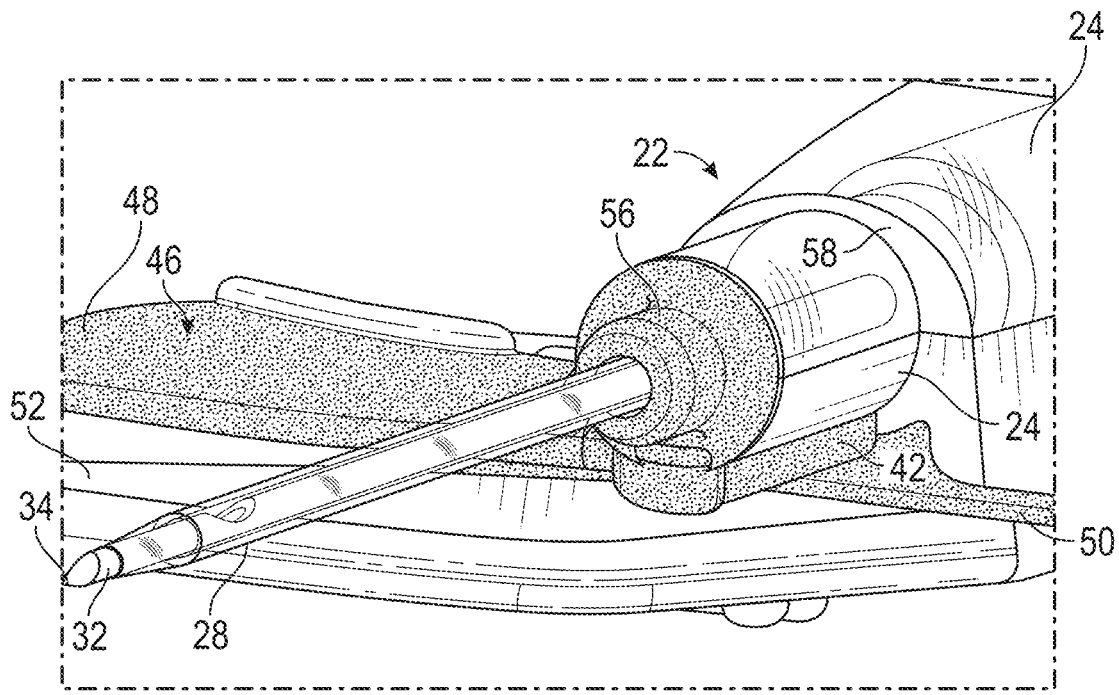
FIG. 3A is an upper perspective view of an example distal end of the catheter assembly of FIG. 2A, illustrating the needle cover removed, according to some embodiments.
Figure 3B:
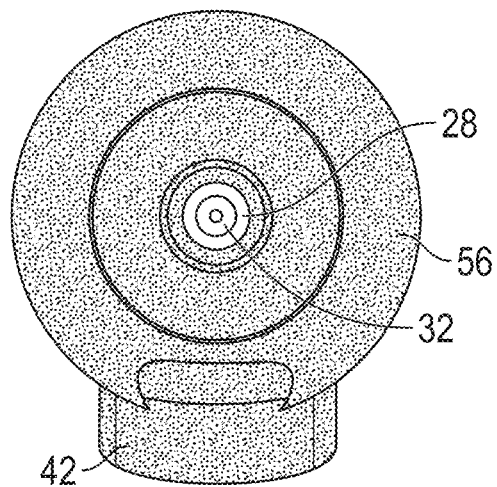
FIG. 3B is a cross-sectional view of the catheter assembly of FIG. 2A along the line 3B-3B of FIG. 3A, according to some embodiments.

Referring now to FIG. 3A-3B, in some embodiments, a strain relief rib 42 may be disposed on the nose 26. In some embodiments, the strain relief rib 42 may be constructed of a compliant or flexible material, which may be illustrated with a dot pattern in the present disclosure. In some embodiments, the inner surface 40 of the needle cover 36 may be smooth and may contact the strain relief rib 42. In some embodiments, the strain relief rib 42 may allow a size of the needle cover 36 to be reduced, compared to the prior art needle cover 10, and also may allow the nose 26 to be small, while facilitating securement of the needle cover 36 to the catheter adapter 22.

In some embodiments, the flexible material may include an elastomer. In some embodiments, the flexible material may include a thermoplastic elastomer. In some embodiments, the nose 26 may be constructed of a rigid or semi-rigid material. For example, the nose 26 may include copolyester, plastic, or another suitable material. In some embodiments, the flexible material may have a higher coefficient of friction with respect to a material of the needle cover 36 than the rigid or semi-rigid material. In some embodiments, the needle cover 36 may be constructed of the rigid or semi-rigid material or another suitable material.

In some embodiments, the strain relief rib 42 may be generally aligned with a longitudinal axis 44 (illustrated, for example, in FIG. 2A) of the catheter adapter 22. In some embodiments, the strain relief rib 42 may be disposed on a bottom of the catheter adapter 22, as illustrated, for example, in FIG. 3A. In some embodiments, the strain relief rib 42 may relieve bending strain on the catheter 28 when the catheter 28 is inserted into the vasculature of the patient. In some embodiments, a bevel of the introducer needle 32 may point upward or away from the bottom of the catheter adapter 22, as illustrated, for example, in FIG. 3A.

In some embodiments, the catheter adapter 16 may include any suitable catheter adapter. In some embodiments, the catheter adapter 16 may include a securement platform 46, which may include a first wing 48 and/or a second wing 50. In some embodiments, the first wing 48 may overlie a grip 52, which may extend from the needle assembly 30. In some embodiments, the grip 52 and/or the second wing 50 may contact and rest upon the skin of the patient when the catheter 28 is inserted into skin of the patient. The bottom of the catheter adapter 22 may be configured to face the skin of the patient when the catheter 28 is inserted into skin of the patient. In some embodiments, the catheter adapter 16 may not include the securement platform 46 and/or the grip 52. In some embodiments, the catheter adapter 16 may be integrated, having an integrated extension tube 54, as illustrated, for example, in FIG. 2A. In other embodiments, the catheter adapter 16 may not include the integrated extension tube 54.

In some embodiments, a distal end of the nose 26 may include a strain relief element 56, which may at least partially surround the introducer needle 32 and/or the catheter 28. In some embodiments, the strain relief element 56 may be constructed of the flexible material or another flexible material. In some embodiments, the catheter adapter 22 may include a stop 58 configured to prevent proximal movement of the needle cover 36 beyond the stop 58. In some embodiments, the stop 58 may include a flange or stepped surface. In some embodiments, the stop 58 may be angled or perpendicular to the longitudinal axis 44. In some embodiments, the stop 58 may be proximate and proximal to the nose 26. In some embodiments, the strain relief rib 42 may extend from the strain relief element 56 to the stop 58.

Figure 3C:
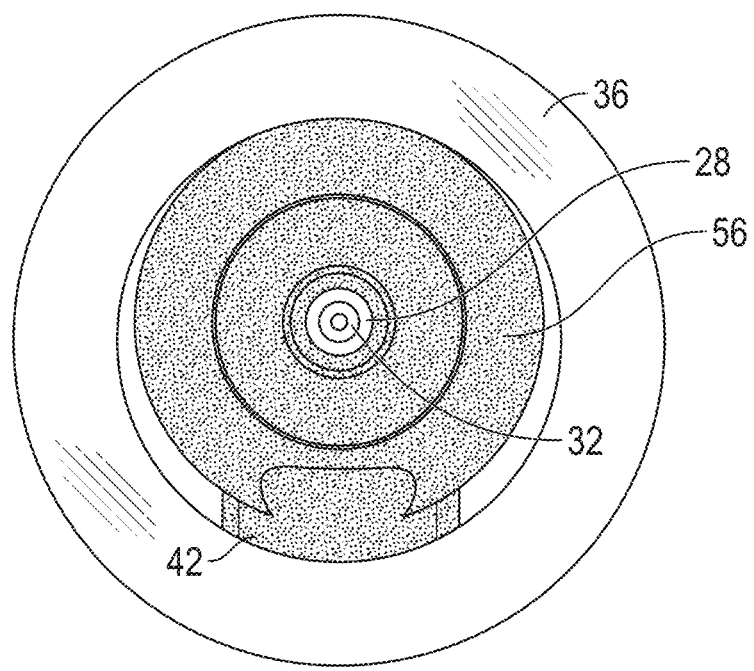
FIG. 3C is a cross-sectional view of the catheter assembly of FIG. 2A along the line 3C-3C of FIG. 2A, according to some embodiments.
Figure 3D:
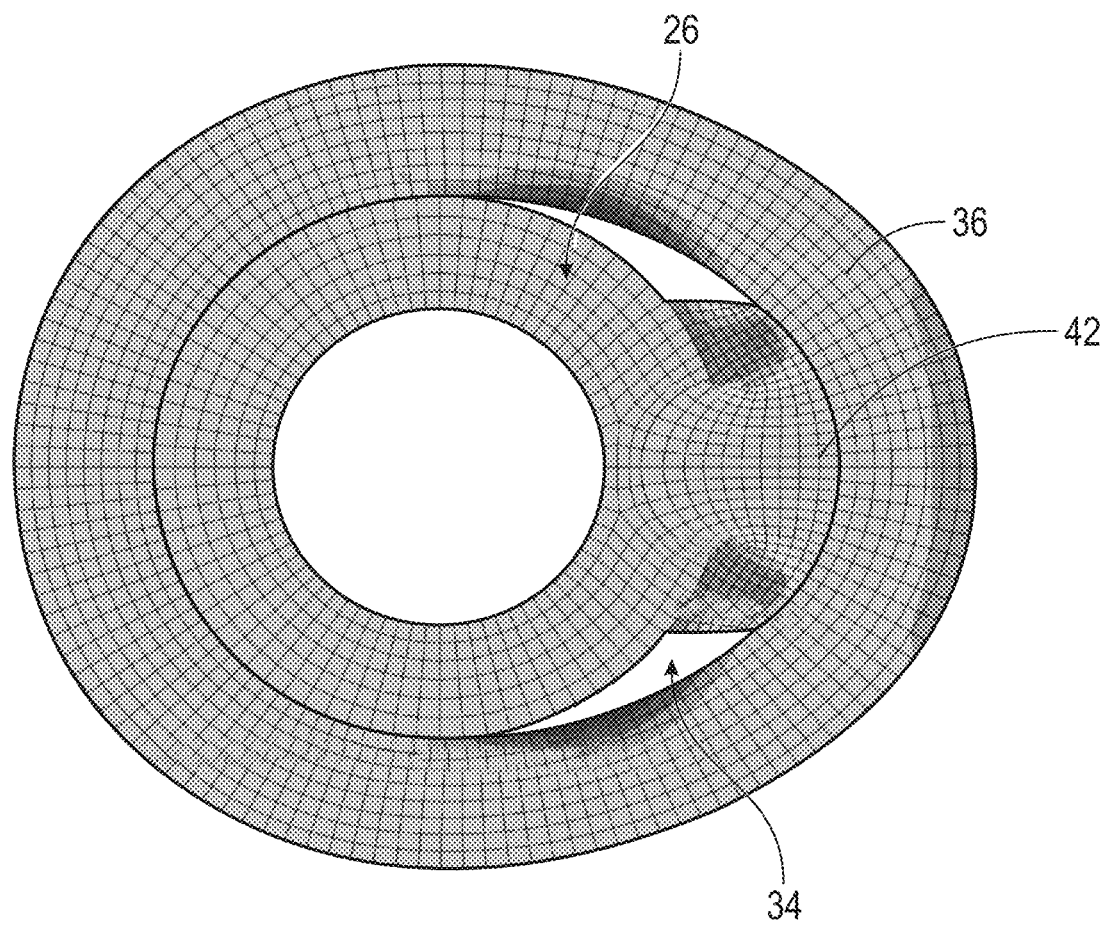
FIG. 3D is an example finite element analysis of a portion of the cross-sectional view of FIG. 3C, according to some embodiments.

Referring now to FIG. 3C-3D, in some embodiments, the needle cover 36 may be removably coupled to the distal end of the catheter adapter 22 via a friction fit. In some embodiments, the needle cover 36 may be removably coupled to the nose 26 of the catheter adapter 22 via a friction fit. In these embodiments, friction between the strain relief rib 42 and the needle cover 36 may retain the needle cover 36 over the distal tip 34 of the introducer needle 32. In some embodiments, the strain relief rib 42 may be compressed when the needle cover 36 is removably coupled to the nose 26 via a friction fit.

FIG. 3D illustrates that the needle cover 36 may experience a flexing beam effect as opposed to an annular hoop stress, which may occur if the catheter assembly 20 included a flexible ring extending around an outer circumference of the nose 26. The flexing beam effect may occur at areas of the inner surface 40 of the needle cover 36 that do not contact the strain relief rib 42 or the nose 26, as illustrated, for example in FIG. 3D. A disadvantage to an annular press fit of two cylindrical bodies, such as the needle cover 36 and the flexible ring, is that with typical molding tolerances, a difference between a least material condition interference and a maximum material condition interference may be as high as ten times.

Figure 4A:
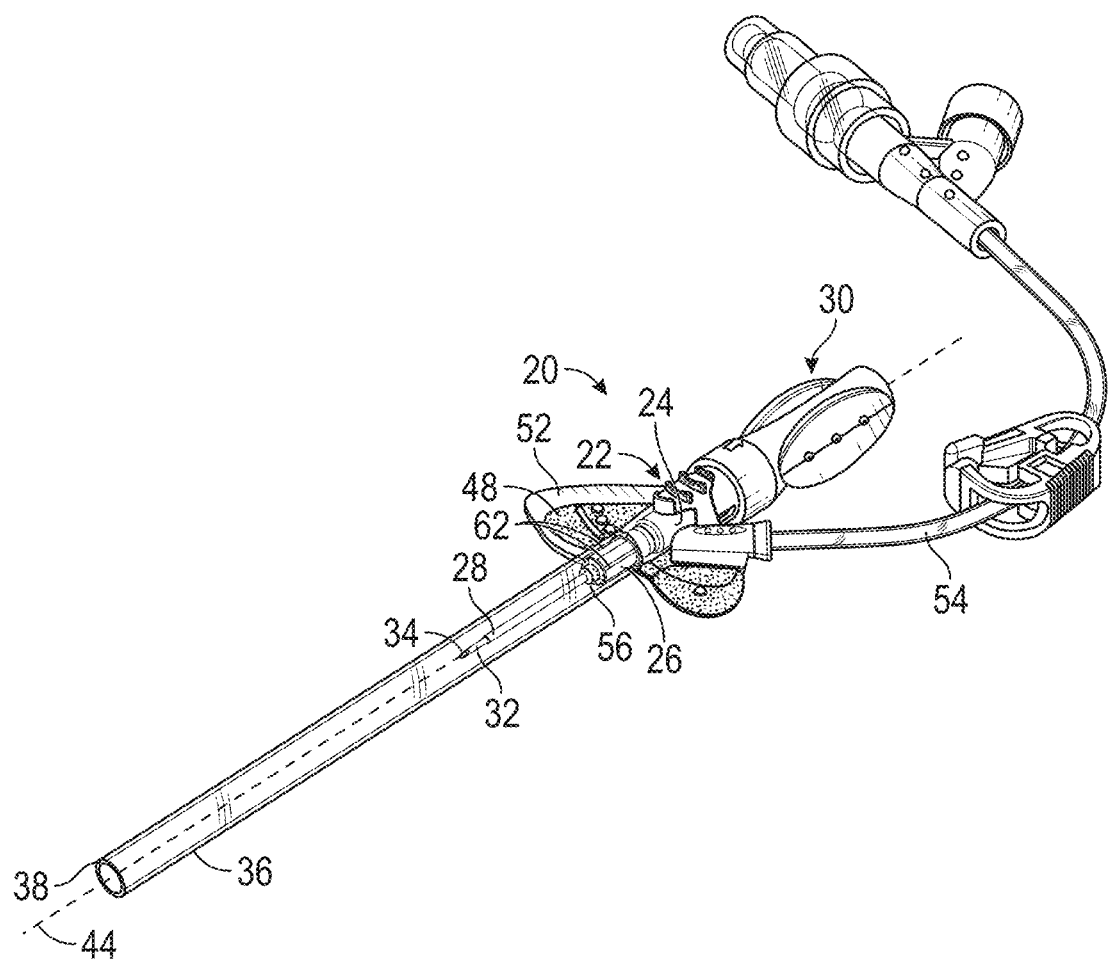
FIG. 4A is an upper perspective view of another example catheter assembly, according to some embodiments.

Referring now to FIG. 4A, another catheter assembly 60 is illustrated, according to some embodiments. In some embodiments, the catheter assembly 60 may include or correspond to the catheter assembly 20. In some embodiments, the catheter assembly 60 may include one or more features of the catheter assembly 20 and/or the catheter assembly 10 may include one or more features of the catheter assembly 60.

In some embodiments, in addition or as an alternative to the strain relief rib 42, one or more other strain relief ribs 62 may be disposed on the nose 26. In some embodiments, the other strain relief ribs 62 may include one or more features of the strain relief rib 42. In some embodiments, the other strain relief ribs 62 may be constructed of the flexible material or another flexible material. In some embodiments, the inner surface 40 of the needle cover 36 may contact and compress the other strain relief ribs 62 to secure the needle cover 36 over the distal tip 34 of the introducer needle 32 in a friction fit.

Figure 4B:
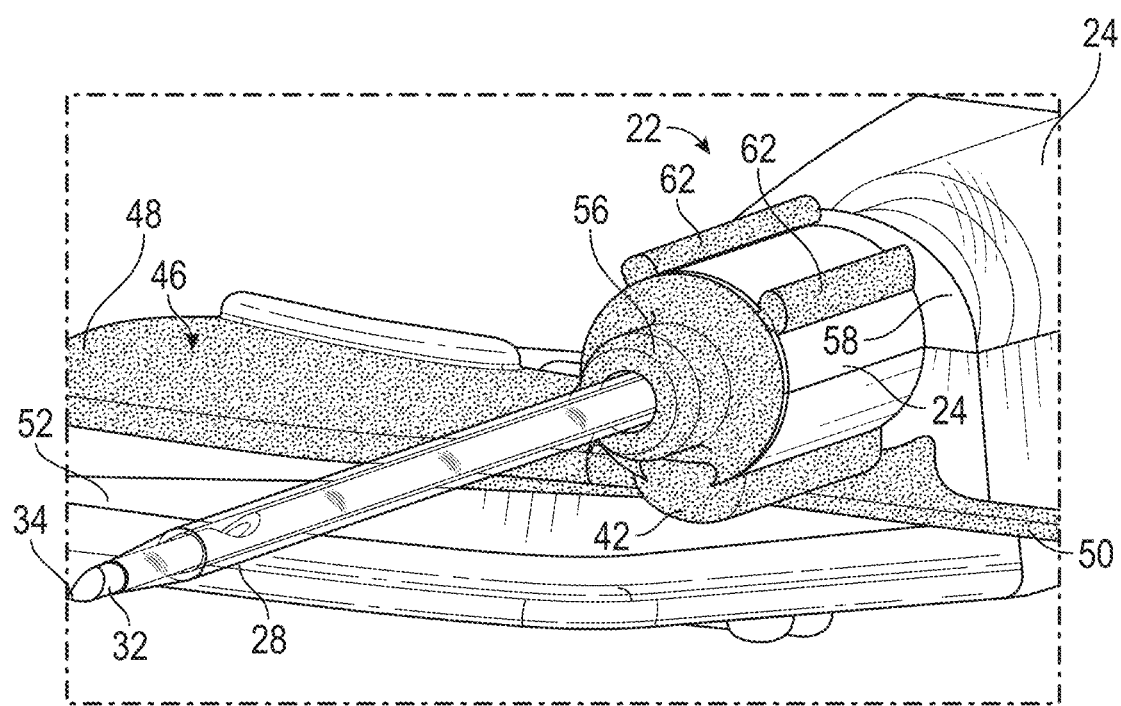
FIG. 4B is an upper perspective view of an example distal end of the catheter assembly of FIG. 4A, according to some embodiments.
Figure 4C:
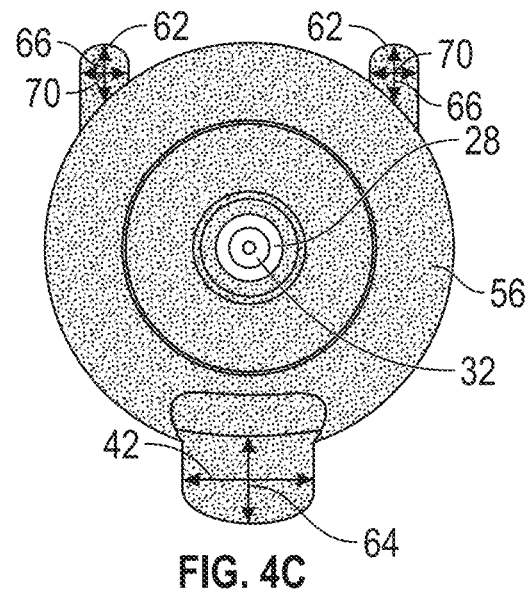
FIG. 4C is a cross-sectional view of the catheter assembly of FIG. 4B along the line 4C-4C of FIG. 4B, according to some embodiments.
Figure 4D:
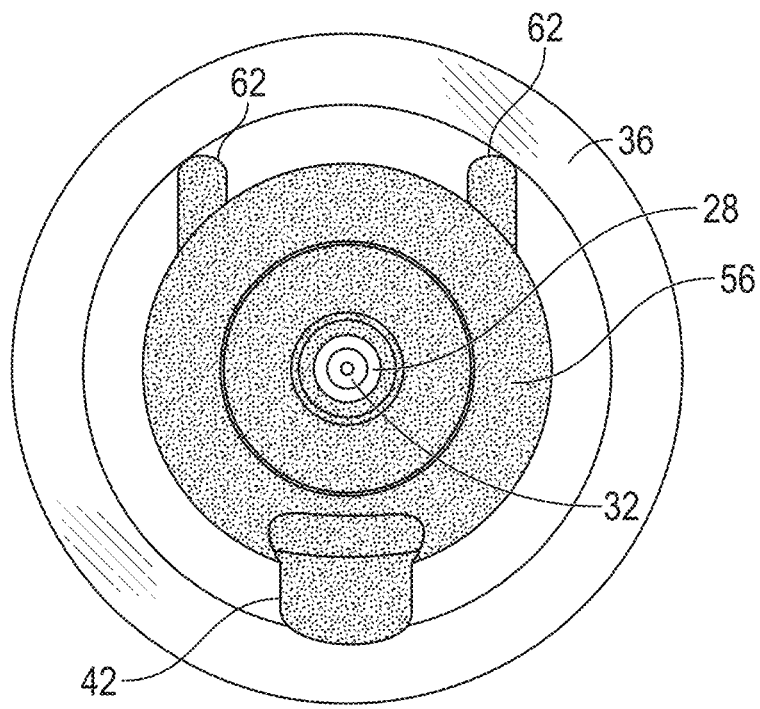
FIG. 4D is a cross-sectional view of the catheter assembly of FIG. 4A along the line 4D-4D of FIG. 4A, according to some embodiments.
Figure 4E:
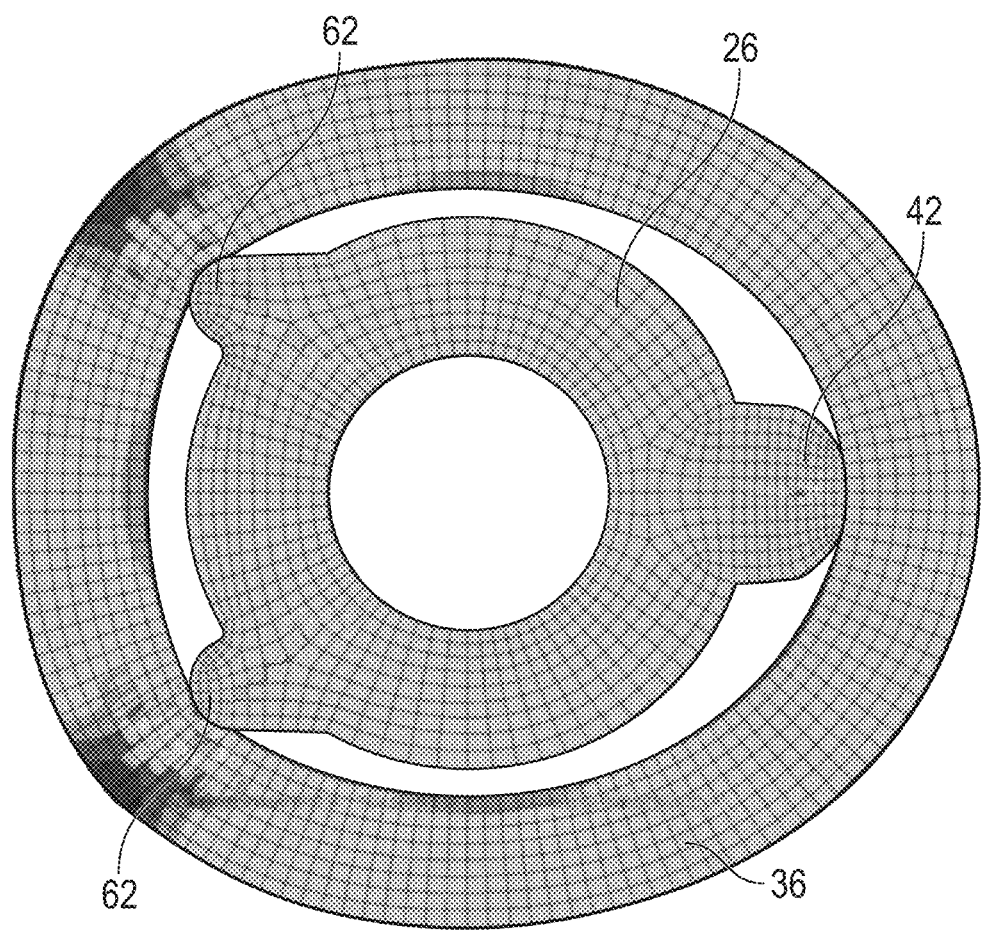
FIG. 4E is an example finite element analysis of a portion of the cross-sectional view of FIG. 4D, according to some embodiments.

In some embodiments, the other strain relief ribs 62 may be aligned with the longitudinal axis 44 of the catheter adapter 22. In some embodiments, one or more of the other strain relief ribs 62 may be disposed on an opposite side of the nose 26 as the strain relief rib 42. In some embodiments, one or more of the other strain relief ribs 62 may be disposed on a top of the nose 26, as illustrated, for example, in FIG. 4B.

In some embodiments, the nose 26 and the strain relief rib 42 and/or the other strain relief ribs 62 may be constructed in at least a two shot mold. In some embodiments, a first hard shot may form the nose 26 in a rigid or semi-rigid material, and a second soft shot may form the strain relief rib 42 and/or the other strain relief ribs 62 in the flexible material.

In some embodiments, one or more of the other strain relief ribs 62 may extend from the strain relief element 56 to the stop 58. In some embodiments, the strain relief rib 42 may be larger than the other strain relief ribs 62. In further detail, in some embodiments, a height 64 of the strain relief rib 42 may be greater than a height 66 of the other strain relief ribs 62. Additionally or alternatively, in some embodiments, a width 68 of the strain relief rib 42 may be greater than a width 70 of the strain relief ribs 62. The height 64 and the height 66 may be measured from the nose 26 to an outer most edge of the strain relief rib 62 and the other strain relief ribs 62, respectively, perpendicular to the longitudinal axis 44. In some embodiments, the other strain relief ribs 62 and the strain relief rib 42 may be approximately a same size.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising:
a catheter adapter comprising a body that forms a distally oriented stop, a nose extending distally from the distally-oriented stop, a strain relief element formed around a distal end of the nose, and a catheter that extends distally from the nose, wherein the nose is generally cylindrical and the strain relief element is formed of a flexible material;
a first strain relief rib disposed on a bottom of the nose, a second strain relief rib disposed on the nose, and a third strain relief rib disposed on the nose, wherein each of the first strain relief rib, the second strain relief rib, and the third strain relief rib extends along a longitudinal axis of the catheter adapter from the strain relief element to the distally-oriented stop and has a height from a circumference of the nose, the height of the first strain relief rib being greater than the height of the second strain relief rib and the height of the third strain relief rib;

a needle secured within the catheter adapter and extending through the strain relief element and the catheter;

a needle cover removably coupled around the nose of the catheter adapter, wherein an inner surface of the needle cover contacts and compresses the first strain relief rib, the second strain relief rib, and the third strain relief rib to thereby secure the needle cover to the nose.

2. The catheter assembly of claim 1, wherein the flexible material comprises an elastomer.

3. The catheter assembly of claim 1, wherein the flexible material comprises a thermoplastic elastomer.

4. The catheter assembly of claim 1, wherein the nose is constructed of a rigid or semi-rigid material.

5. The catheter assembly of claim 1, wherein the strain relief element is disposed on a distalmost surface of the nose.

6. The catheter assembly of claim 1, wherein the distally-oriented stop is configured to prevent proximal movement of the needle cover.

7. The catheter assembly of claim 1, wherein the catheter adapter includes a securement platform.

8. The catheter assembly of claim 7, wherein the securement platform comprises a first wing and a second wing.

* * * * *